United States Patent [19]

Erb

[11] Patent Number: 4,494,540

[45] Date of Patent: Jan. 22, 1985

[54] UNIVERSAL MICROSLAD

[76] Inventor: Robert C. Erb, 433 Brockmont Dr., Glendale, Calif. 91202

[21] Appl. No.: 438,612

[22] Filed: Nov. 2, 1982

[51] Int. Cl.³ .............................................. A61B 17/36
[52] U.S. Cl. ................................ 128/303.1; 128/305; 219/121 L; 219/121 LU
[58] Field of Search ...................... 128/395, 396, 303.1; 350/486; 219/121 L, 121 LB, 121 LU, 121 LV

[56] References Cited

U.S. PATENT DOCUMENTS

| | | | |
|---|---|---|---|
| 3,467,099 | 9/1969 | Lotmar | 219/121 L X |
| 3,710,798 | 1/1973 | Bredemeier | 249/121 L X |
| 3,782,823 | 1/1974 | Kantorski et al. | 219/121 L X |
| 3,893,447 | 7/1975 | Hochheimer et al. | 128/303.1 X |
| 3,930,504 | 1/1976 | de Laforunde | 128/303.1 |
| 4,091,814 | 5/1978 | Togo | 128/303.1 |
| 4,141,362 | 2/1979 | Wurster | 128/303.1 |
| 4,228,341 | 10/1980 | Zandberg | 219/121 LU X |
| 4,289,378 | 9/1981 | Reny et al. | 128/303.1 X |
| 4,396,285 | 8/1983 | Presta et al. | 128/303.1 X |
| 4,397,310 | 8/1983 | Pomerantzeff | 128/303.1 |

Primary Examiner—Edward M. Coven
Attorney, Agent, or Firm—Frank L. Zugelter

[57] ABSTRACT

A device (10) for directionally controlling a beam of light, particularly adaptable with a laser beam in surgical operations. The beam is focused in a chamber (10) by a lense (46) (one of a selectable number), passes through a passageway (16) through which the operator or surgeon observes the target area for the beam, and strikes a specular element or mirror (27) in a cavity (26) separated from the chamber (12) by the passageway (16). The disposition of the mirror (27) in the cavity eliminates vignette obstructions of such element that heretofore was disposed in the passageway in prior teachings. The beam reflects from the mirror (27) in the direction of the target. A unique joystick (28) is operatively connected to the mirror (27) to swivel same and thereby control the direction of the beam. The device (10) is mounted to an adaptor (20) for 360° rotation thereabout. A unique means (22) to universally mount and rotate device (10) to adaptor (20) is provided, with clamping means (23) to stationarily position or lock one to the other at any angle or inclination. Features, such as a nozzle (25) to introduce nitrogen into the chamber (12) to cool the lens (26), scalloped edges (19) about the passageway (16) for conveyance of an instrument from one side of the device to the other, and a rest (86) for the hand or fingers not manipulating the joystick, are included. The feature of universality of rotation is not limited to a device of this type in which the mirror (27) is disposed only in the cavity; such feature is applicable to state-of-the-art devices wherein the mirror (27) is located in the passageway (16).

42 Claims, 9 Drawing Figures

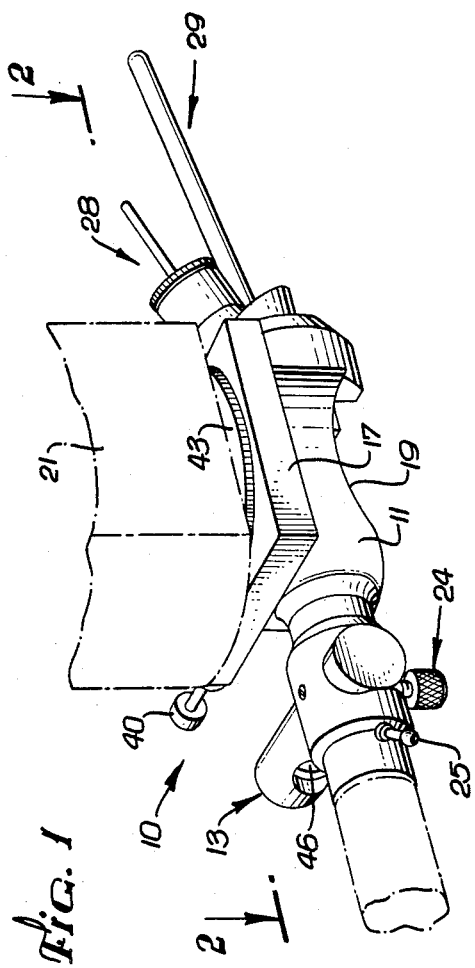
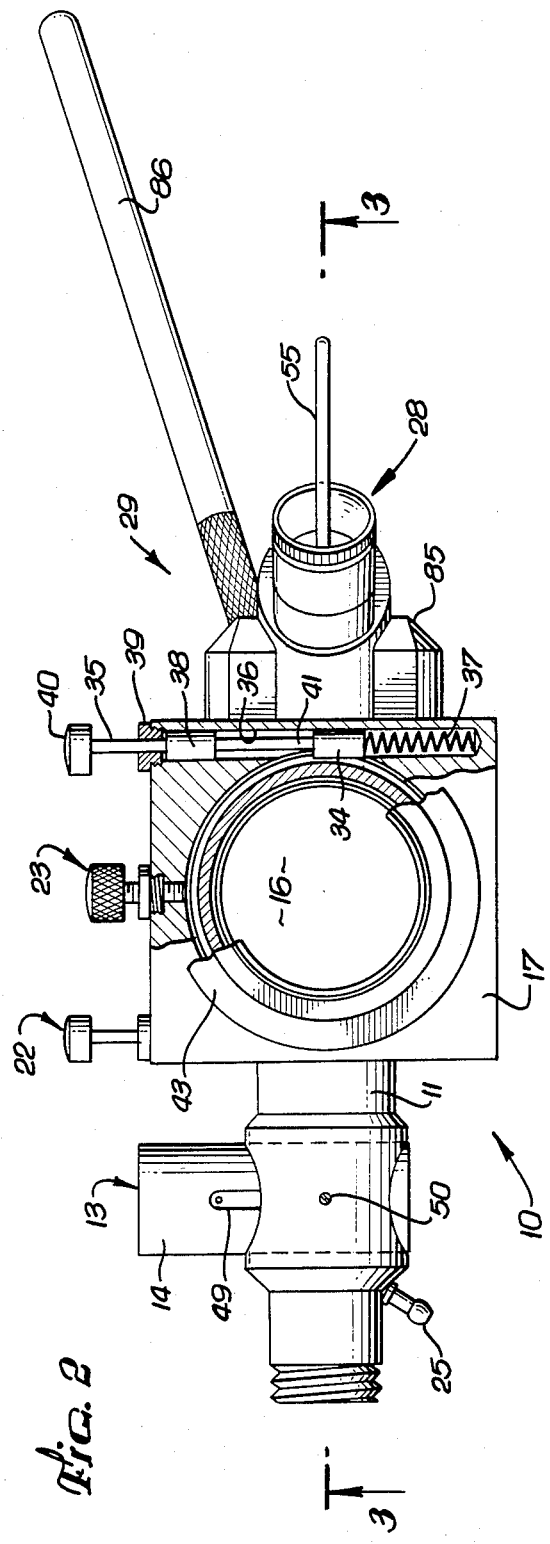

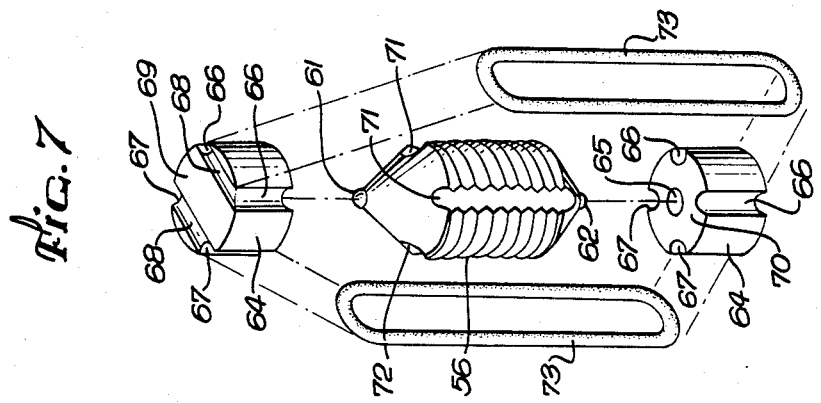
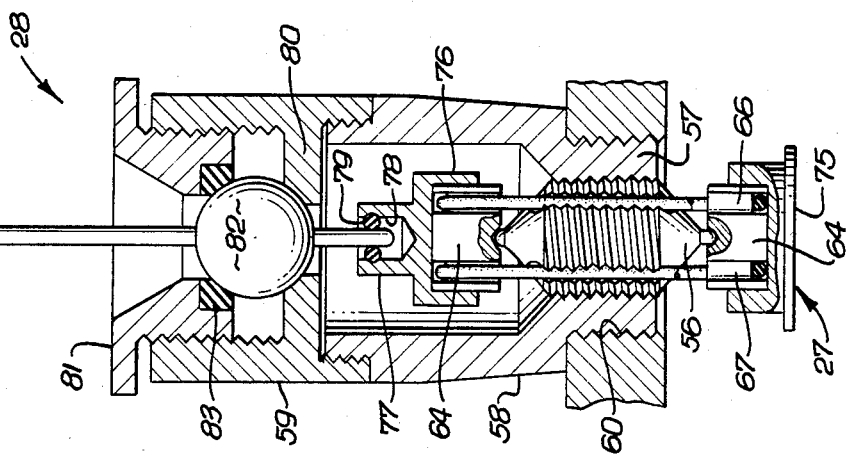
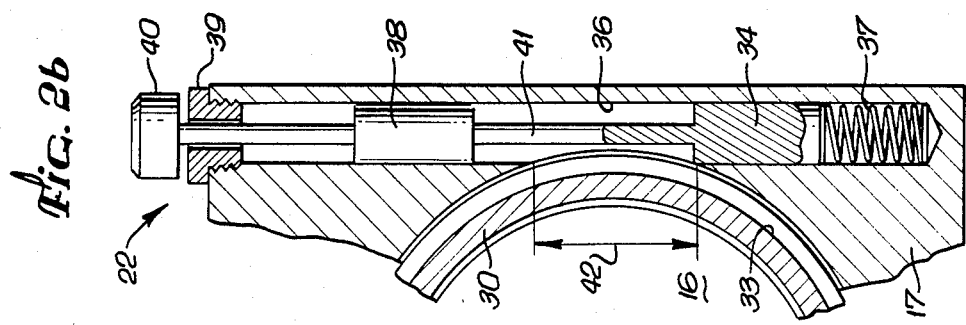
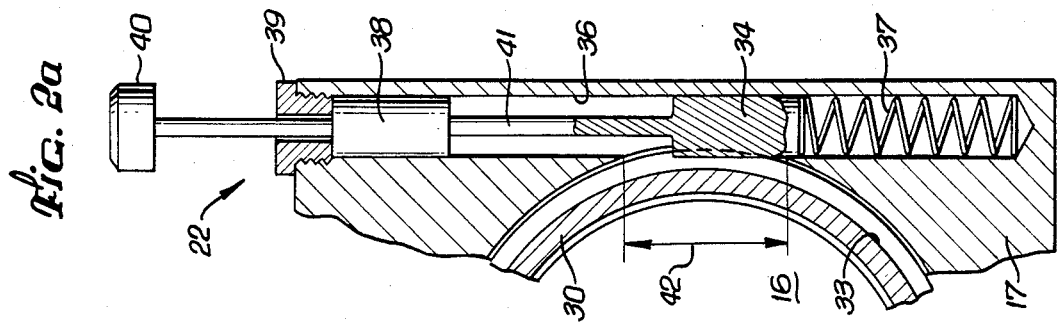

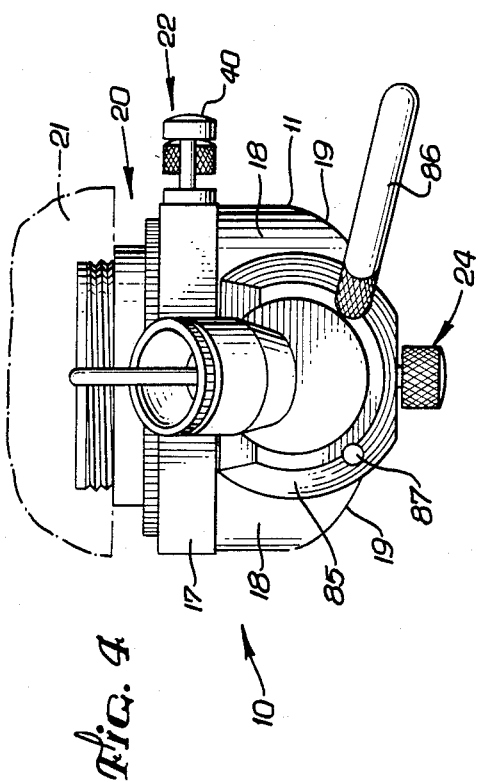
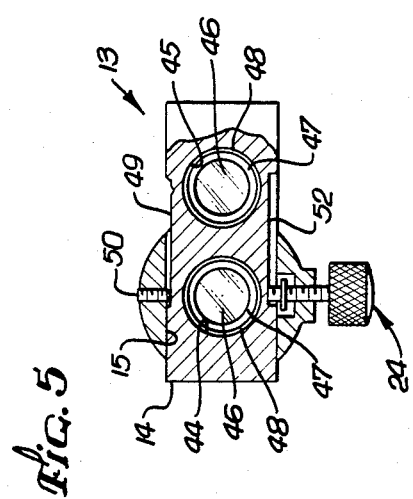
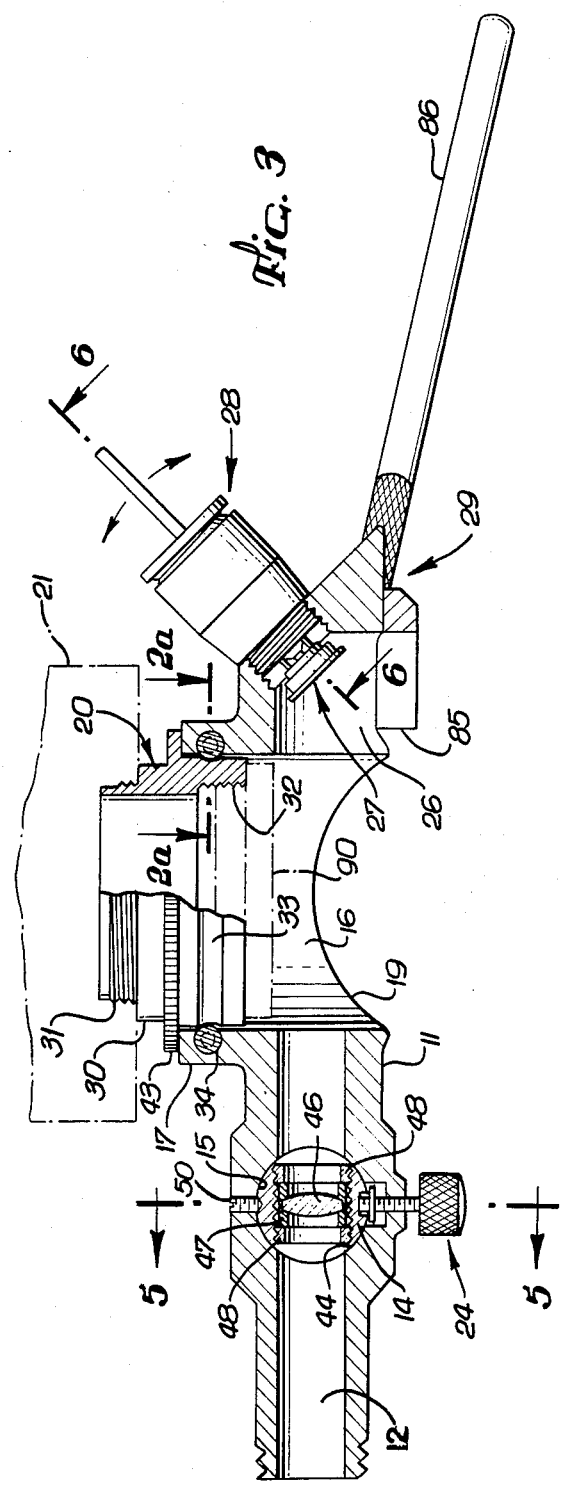

UNIVERSAL MICROSLAD

TECHNICAL FIELD

This invention relates to cutting, sealing, or surgical devices, and more particularly to a device performing delicate surgical operations on or in the human body with the use of a directionally-controlled laser beam.

BACKGROUND ART

See: U.S. Pat. Nos. 3,528,424; 3,703,176; 3,710,798; 3,783,874; 3,796,220; 3,865,114; 4,141,362; 4,228,341.

DISCLOSURE OF INVENTION

Successful use of a laser beam device in a surgical operation has been primarily dependent upon its adaptation to a microscope through which a surgeon observes and acts upon the target area to be affected by the laser beam. However, the specular element off of which the laser beam is transmitted to the target area has, in prior devices, interfered with the line of sight or view for the surgeon to the target area. In observation through his microscope, the surgeon sees a vignette, i.e., a shadowing or infringing upon the optical axis of the microscope's lens by such specular element, thus, impairing his view. Also, the fixation of the device upon a microscope limits a surgical operation to one surgeon, leaving other observing surgeons to merely observe rather than to participate; or if another or other surgeons do participate in the actual surgery being performed, they are limited to the fixation of the device to the microscope as was set by the first surgeon.

This invention provides a clear, unobstructed line of sight or view for a surgeon, as the device embodying the invention carries the specular element outside the optical axis for the microscope's lens. Further, the device embodying the invention includes a universal rotational feature by which it can be rotated about such lens, for the particular orientation desired by any surgeon or user.

This invention eliminates all physical obstructions between the microscope's lens and the target area; and provides a universality of rotational adjustment for any device embodying it whether this novel device or an old one.

An object of this invention is to provide a new or improved device for directionally controlling a beam of light as it is transmitted from the device.

Another object of the invention is to provide an unobstructed view for the field or line of sight for a surgeon to the target area, thus rendering a clear view of such area.

Still another object of the invention is to provide a universality of rotational ability to such device, about the axis of the optical lens of the microscope.

A further object of the invention is to provide a rest for a user or surgeon's hand or fingers operating the device while changing the direction of the beam eminating from the device.

Another object of the invention is to provide a facility of ease in transferring an instrument from one side of the device to the other, desired, for example, by another user moving into position behind the microscope to perform surgery with his hand other than the same hand of the first user's or surgeon's.

Another object of this invention is to provide facility of participation by several users or surgeons by reason of the universal mountability of a device for directionally controlling a laser beam upon a microscope.

Another object of this invention is to provide a novel joystick mechanism for manipulating the plane of a specular element off of which a beam is bounced or reflected.

These and other objects and advantages of the invention will become more apparent by a full and complete reading of the following description, appended claims thereto, and the accompanying drawing comprising three sheets of Figures.

BRIEF DESCRIPTION OF THE DRAWING

FIG. 1 is a perspective view of a device embodying the invention, shown in operative connection to a surgeon's microscope.

FIG. 2 is a view taken on line 2—2 of FIG. 1.

FIG. 2a is a magnified view of a portion of FIG. 2.

FIG. 2b is a modified view of FIG. 2a.

FIG. 3 is a view taken on line 3—3 of FIG. 2.

FIG. 4 is a right end view of the device shown in FIG. 2.

FIG. 5 is a view taken on line 5—5 of FIG. 3.

FIG. 6 is an enlarged cross-sectional view of a joystick mechanism included in the disclosure the operation of which controls the direction of transmission of a light beam as it eminates from the device.

FIG. 7 is an exploded perspective view of elements included in the mechanism illustrated in FIG. 6.

BEST MODE OF CARRYING OUT THE INVENTION

Referring now to the accompanying drawing comprising three sheets of FIGURES on which reference characters therein correspond to like numerals hereinafter, numeral 10 [FIG. 1] identifies a device or apparatus or manufacture embodying the invention. This type of device is usually referred to as a "Microslad". Device 10 generally comprises a housing 11 having a chamber 12 [FIG. 3] extending along a generally longitudinal length open to atmosphere at its one terminus for suitable connection to a source (not shown) for a laser beam. Proximate such open terminus a lens means 13, such as a multiple-lens cylinder 14 slip-fitted to a bore 15 disposed crosswise of chamber 12 in housing 11, is suitably mounted. A passageway 16 intersects chamber 12 at the latter's other end, the passageway 16 being open to atmosphere at both of its termini. Passageway 16 is formed preferably from and in the material of housing 11, and includes a body portion 17 proximate its one or upper terminus and walls 18, preferably arcuate in nature, proximate its other or lower terminus. Opposing edges 19 in walls 18, as best seen in FIGS. 3, 1, are scalloped in their formation, for a purpose more fully described hereafter. A means 20 for adapting device 10 to, say, a surgeon's microscope 21 (in phantom), is provided for operable connection of device 10 to microscope 21, as well as providing universal rotational ability for device 10, about the optical axis for microscope 21, in its cooperative relationship to elements in device 10, more fully described hereafter. A means 22 attaches in a universal manner adaptor 20 to housing 11 and is included in body portion 17, while a means 23 [FIG. 2] to clamp adaptor 20 in a stationary manner to housing 11 is mounted on body portion 17. In this particular embodiment, a similarly constructed means 24 [FIG. 5] is mounted on housing 11 to clamp the slidable lens cylinder 14 in a stationary manner in its bore 15, while a nozzle 25 [FIGS. 1, 2] for introducing nitrogen to cool lens means 13 is securely mounted on housing 11 proximate the disposition of element 13.

A cavity 26 is provided in housing 11 in alignment with chamber 12 but at the other extreme dimension for the intersecting passageway 16, as seen in FIG. 3. I.e, passageway 16 separates cavity 26 from chamber 12. Cavity 26 is open to atmosphere in the same general direction as is the lower terminus for passageway 16. A specular element or means 27 is suitably disposed and mounted in cavity 26 for reflecting a beam of light from the interior of housing 11 to its exterior or atmosphere. A joy-stick mechanism 28 is adjustably mounted to housing 11, being operatively connected to specular element 27, whereby the direction of the beam from element or mirror 27 to atmosphere is controlled. A finger or hand rest 29 [FIGS. 2, 3, 4] is releasably mounted on the end of housing 11 nearest which the joy-stick mechanism 28 is mounted and disposed.

In more particularity, housing 11 is preferably formed as a one-piece lightweight metallic manufacture, preferably integrally including chamber 12, passageway 16, and cavity 26. Passageway 16 extends in a vertical manner, its axis perpendicular to the axis for chamber 12, and includes as part of its formation the marginal, preferably rectangular, body portion 17 and the walls 18 which are preferably generally arcuate in nature. The bottom edges 19 of walls 18 are scalloped [FIGS. 1, 3] such scalloping providing for direct transfer from one hand to another an instrument or the like during use of the invention. The inner wall surfaces for body portion 17 are circular in nature to accomodate and complement the preferred circular formation for adaptor 20. Means 20 comprises a circular member 30 formed of a lightweight metal material, having an externally threaded one end 31 [FIG. 3] and an internally threaded other end 32. An annular groove 33 is formed in the exterior wall of circular member 30, opposite the internally threaded end 32, for cooperation and engagement with the means 22 to attach in a universal manner adaptor 20 to housing 11. In this embodiment a pair of such means 22, spaced from each other, is shown, and each thereof comprises [FIGS. 2, 2a, 2b] a piston 34 formed at the end of a shaft 35, the piston being slidably mounted in a bore 36 formed in body portion 17. Piston 34 is biased to a particular normal position in bore 36 by means of ccoperation between a coiled spring 37 disposed in the bottom of bore 36 and a stop element 38 included along the shaft 35 cooperating with a collar member 39 threaded to the mouth of the bore 36. Shaft 35 projects out of bore 36 so that a finger button 40 securely mounted on its end can be depressed to thereby change the position of piston 34 along bore 36 and against the action of biasing spring 37. It is to be noted that shaft 35 is reduced in its diameter in its section 41 disposed between piston 34 and stop element 38 for a purpose more fully described below.

Piston 34 of each means 22 cooperates with annular groove 33 of circular member 30 by engaging it and disengaging it, thus locking and releasing adaptor 20 to and from housing 11. To perceive either of such actions, engagement or disengagement, we look to FIGS. 2a and 2b which are magnified views of the pertinent portions of device 10 that show such respective actions. Diametrical and volumetrical dimensions of passageway 16 intersect the bore 36 to some extent; per FIG. 2a. Consequently, an open slot of length 42 contributes to the forming of the marginal body portion 17 of housing 11, such slot being in general planar relationship with the plane of annular groove 30. When no obstruction, such as piston 34, is disposed in bore 36 along length 42, per FIG. 2b, the full circumference of circular member 30 can pass through that volumetric portion of bore 36 lying co-extensive with the slot of length 42. Thus, by depressing both finger buttons 40, each piston 34 is cause to displace in its corresponding bore 36, compressing its corresponding spring 37, and to no longer be an obstruction along the length 42. Only the reduced section 41 of each shaft is co-extensive or greater in its length with slot length 42 and is disposed physically outside of the circumferential fullness of circular member 30. Circular member 30 can thence be introduced into passageway 16 or be released therefrom during such displacement. Releasing finger buttons 40 again installs the respective pistons 34 in their respective bores along corresponding lengths 42, per FIG. 2a, i.e., in their normally biased positions. Circular member 30 properly sets in passageway 16 by reason of a ring 43 [FIGS. 2, 3] integrally formed on and about member 30, being flush upon body portion 17. With piston 34 in its normally biased position, thus within the volumetric fullness of passageway 16, adaptor 20 is locked to housing 11, however, retaining the ability to universally rotate in and about passageway 16 and microscope 21, and vice versa, as will become apparent. Without depression of buttons 40, adaptor 20 cannot be introduced into passageway 16 for locking to housing 11, nor can adaptor 20 be removed from housing 11 were it universally rotatably locked therein in the first place, without depression of finger buttons 40.

Clamping means 23 is mounted on an exterior wall of marginal body portion 17 [FIG. 2] and comprises a conventional thrum-screw element securely mounted on a screw-shaft threaded into and through body portion 17 so that its free end is capable of being projected into passageway 16. Such free end clamps against annular groove 33 in circular member 30 to thereby stationarily position adaptor 20 to device 10.

Lens means 13 preferably comprises [FIGS. 1, 2, 3, 5] a lightweight metal cylinder 14 having a pair of parallel threaded bores 44, 45 passing therethrough at right angles to its major axis, with a lens 46 retained in each bore 44, 45. Each lens 46 is suitably secured in a circular retainer 47 which itself is threaded to a corresponding bore 44, 45. Threaded apertured rings 48 in cylinder 14 are tightened down on each side of and against their corresponding retainer 47 for each lens 46.

An elongated depression 49 extends longitudinally or peripherally along the exterior wall of cylinder 14, in a plane coincident to the plane for the lens 46, for cooperation with a small set screw 50 extending downwardly [FIG. 5] through housing 11 so that cylinder 14 does not rotate in its bore 15 formed in and cross-wise of housing 11, but does remain slidable to-and-fro therein to the extent of the length of depression 49. A similar depression 52 is disposed at the opposite extreme of the arcuate wall of cylinder 14, for cooperation with means 24 to clamp cylinder 14 in a particular stationary position in housing 11. The depressions 49, 52 lie in the same vertical plane, and assure vertical positioning for each one of the lens 46 in chamber 12. The extreme termini for each depression 49, 52 in conjunction with clamping means 24, assures proper alignment or centering of each lens 46 relative to chamber 12. Clamping means 24 comprises a similar or like element to that of means 23, and which is well known in the arts for effecting a tightening function on depression 52 in cylinder 14.

FIGS. 6 and 7 disclose in detail a "joy stick" mechanism 28 for supporting and operating a joystick proper or lever 55 by which a beam's direction is controlled upon and after striking specular element 27 in cavity 26 and being reflected therefrom to atmosphere. Mechanism 28 comprises a threaded core member 56, preferably of plastic material, which complements threads interiorly mounted in a neck 57 of the lower of two securely-held together circular sleeves 58, 59. The exterior wall of neck 57 in turn is threaded as at 60, to complement a threaded opening in the end of housing 11 proximate the cavity 26 [FIG. 3]. Core 56 is conically formed at its both ends to form swivel or rocking fulcrums 61, 62 each of which cooperating with a corresponding one of a pair of symetrically formed lightweight metal motion members 64 which include centered depressions 65 which ride on or are supported by such corresponding fulcrums 61, 62. Each motion member 64 includes pairs or peripheral channels 66, 67 formed in and extending along its surface. Each pair of channels 66, 67 is connected by a chordal channel 68 formed in an end face 69 of each member 64, which end face 69 opposes the end face 70 on the same member 64 in which its depression is formed.

Pairs of channels 71, 72 are formed along and in the peripheral length of core 56 for alignment with channels 66, 67, respectively, in the members 64. Each of a pair of looped members 73, preferably piano wire brazed together by known micro-welding processes, although conventional O-ring rubber may be used, engages or seats in a corresponding pair of chordal channels 68 and a correspair of channels 66, 67 in members 64, and a corresponding pair of peripheral channels 71, 72 in core 56 so as to hold together in an assembled fashion the elements shown in FIG. 7. Or, ends of each member 73 may be suitably fixed to specular element 27. See such elements in assembled relationship in FIG. 6 in which core 56 is shown to be threaded securely to neck 57 of sleeve 58.

The specular element 27, having a reflective surface 75, is press fit to the one rocker or motion member 64 that is disposed in cavity 26, while a circularly-formed housing 76 having a lower bore is slip fitted to the other motion member 64, all as seen in FIG. 6. The housing 76 includes a head 77 having a chamber 78 opening upwardly to accomodate or cooperate with joy stick proper 55. The one end of lever 55 frictionally engages a small O-ring 79 set within a circumferential groove interiorly of the wall forming chamber 78. The length of lever 55 extends upwardly through an apertured cross-sectional portion 80 formed in sleeve 59 to exit and terminate outwardly of an apertured cap 81 threaded to the free end of sleeve 59.

Apertured portion 80 forms a socket for a spherical ball 82, through which lever 55 extends as shown. Ball 82 is maintained in its position on such socket by means of a resilient (rubber) ring 83 mounted in a circumferential groove provided in cap 81. It is apparent that force applied to ball 82 by tightening cap 81 against sleeve 59 causes less ease in movement of lever 55 as well as preventing it from moving if tightened sufficiently, while loosening cap 81 in sleeve 59 causes more ease in movement of lever 55 as well as providing for free play of lever 55 if loosened too much. With any movement of lever 55 about the center point of ball 82, a motion is accorded housing 76. Such motion produces in turn a swivaling motion for specular element 27, as a result of members 73 reacting to the lever's movement. Precise movement for specular element 27 is achieved by this mechanism 28, however, it should be understood that other joy stick mechanisms, including gimballed ones, can serve the same purpose as mechanism 28 in the operation of this invention.

The rest 29 [FIGS. 2, 3, 4] comprises a generally arcuately-shaped metal member 85 invertedly mounted by way of an exterior slip-fit to housing 11 and in an enveloping relationship about cavity 26. Member 85 is sufficiently rounded in its coupling dimension to housing 11 so that it doesn't fall off of the complementing circular portion of housing 11 to which it slip fits. A stem 86 has its one end (not shown) threaded for fastening into one or the other of two threaded holes 87 [FIG. 4] on a facing side for member 85. Upon such threading, the tightening of stem 86 in either hole 87 forces its end (not shown) to frictionally engage or grip an exterior wall of housing 11 or the complementing circular portions of housing 11 to which it slip fits. Such gripping secures the rest 29 in fixed position for use.

The respective axes for holes 87 lie in compound angular directions from a vertical plane passing through the facing in which holes 87 are located, best observed from FIGS. 3 and 4. Thus, stem 86 is located conveniently for resting a hand or fingers of the surgeon who is operating joy stick lever 55 by the fingers of such hand. This is so for either a right or left handed operator.

In operation, a front lens 90 [FIG. 3, shown in phantom] is first removed from the front end of a surgeon's microscope 21, and is replaced by adaptor 20 the threads 31 of which being threaded to the front end of microscope 21. Front lens 90 is threaded to adaptor 20 as at 32, before or after the latter is attached to microscope 21. Device 10 then is set in one's hand in such a manner that two fingers of the hand depress both finger buttons 40. Thereafter, a body portion 17 is mounted onto circular member 30 of adaptor 20, below its annular ring 43. Since pistons 34 are not within the circumferential diameter or dimensions of the wall forming passageway 16 in this position for buttons 40, adaptor 20 accepts body portion 17 until the latter seats on ring 43. Buttons 43 are released, pistons 34 assume their normally biased positions which now lie within such circumferential diameter or dimensions of passageway 16, and device 10 now is universally rotatably attached to device 10 by reason of pistons riding in groove 33 of adaptor 20. Device 10 is rotatable to any degree about adaptor 20 and microscope 21, as the surgeon who will be using it pleases. Upon rotation to a desired degree or inclination, clamping means 23 is tightened to stationarily clamp device 10 to adaptor 20 and thus to microscope 21.

The open end of chamber 12 is connected (not shown) to a suitable source of a laser beam so that it is caused to travel into chamber 12, through a lens 46 aligned therein and thence through passageway 16 to cavity 26, to strike mirror 75. As the beam strikes reflective surface 75 at an angle of incidence, it accordingly reflects therefrom in cavity 26 to be cast outwardly of device 10 towards and to the target, say, within an opening in the human body and which is being surgically treated by the surgeon operating device 10. The surgeon is optically observing through microscope 21, its lens 90 and passageway 16 such target area free of any obstruction within his line of sight. Manipulation of joystick lever 55, after the surgeon has adjusted cap 81 to achieve a desired tension on such lever, provides for directional control of the beam as it leaves mirror 75. Thus the surgeon can determine what part of the target area the beam will strike. Rest 29, though optional with the acting surgeon, provides support for the hand or other fingers of the hand than that manipulating lever 55.

During the process of introducing a laser beam into chamber 12 and beyond, nitrogen is fed through nozzle 25 into chamber 12 for cooling a lens 46 aligned or centered therein as the beam passes through it.

Scalloped or cut-out edges 19 provide for a direct line of conveyance of an instrument from one hand of an operator to the other hand, thereby minimizing if not eliminating inconvenience to the surgeon during an operation, particularly at a critical moment.

Suitable and well known materials, in various forms of metals such as stainless steel, aluminum, brass and of plastic and rubber, are utilized in the manufacturing of device 10. Known manufacturing processes and techniques are readily available for fabricating the aforesaid described elements, such as by precise machining, turning and other techniques, including computerized programing of cutting for housing 11. Standards for the quality of mirror 75 for surgical purposes are known and practiced in known ways in various arts.

Although known in the practice of surgery, briefly it should be mentioned that microscope 21 is supported by an arm or the like which may be part of an articulated supporting structure known in laser surgical practice and procedure, as well as having a light source introduced into microscope 21 and thence through passageway 16, to light the working or target area on which the laser beam is applied. None of this, of course, constitutes part of the present invention.

In assembly of device 10, the various parts of elements of the embodiment are first produced in known fashion. With bore 36 formed in housing 11, the elements 35–41 are assembled therein with no difficulty. The lenses 46, their retainers 47 and rings 48 are positioned in cylinder 14, after which the latter is introduced into its bore 15. Clamping means 24 and set screw 50 then are threaded to housing 11 as shown in FIG. 3, to ride in their corresponding depressions 52, 49 formed in cylinder 14. Thus cylinder 14 does not escape from its bore 15.

Joy stick 28 is sub-assembled, with specular element 27 as part thereof, prior to introduction of its neck 57 into threads 60 of housing 11. Very simply, the three elements 56, 64 and 64 are mounted upon themselves, as indicated by FIGS. 7 and 6, after which members 73 are brazed, in their corresponding channels of such three elements. Specular element 27 is mounted to the one member 64 and head 76 is mounted to the other member 64. Core 56 is threaded to sleeve 58. Then, sleeve 59 is secured to sleeve 58, spherical ball 82 and its lever 55 then being introduced into sleeve 59, with the one end of lever 55 being introduced into and past O-ring 79 in chamber 78. Thereafter, apertured cap 81 is threaded to sleeve 59 until resilient ring 83 frictionally engages spherical ball 82. Adjustment of tension on lever 55 may be better accomplished after mechanism 28 is securely mounted to housing 11 by threading sleeve 58 to threads 60.

Rest means 29 is quickly assembled to the one end of housing 11 by simply finger slipping element 85 thereon, after which stem 86 is threaded to its hole 87 to secure the element 85 in position by frictionally engaging the exterior of housing 11.

Adaptor 20 may be mounted to body portion 17 before or after it has been mounted to microscope 21. Then, buttons 40 are depressed by one's fingers so that passageway 16 can be introduced onto adaptor 20 below its annular ring 43. The fingers are released from buttons 40, and pistons 34 return to their normally biased positions to rotatably lock housing 11 and adaptor 20 together, and thus likewise to microscope 21. Device 10 is universally rotatable about the optical axis of lens 90 and means 23 clamps device 10 to any desired angle or inclination within 360°.

It is to be understood that the invention perceives of the adaptor 20 being part of a body of a microscope or the like. I.e., the feature of annular groove 33 in adaptor 20, or its equivalent, may be located in the body of a microscope, and need not be necessarily a separate element as is shown in this disclosure. Furthermore, it becomes apparent that the adaptor and housing become first and second elements which may be utilized in any apparatus requiring a universality of rotation and/or means for clamping the elements together where such elements include the aforesaid disclosed features for such purposes.

It should also be understood that various features disclosed herein are not exclusive or limited in their dispositions in the disclosed device 10. For example, the joystick mechanism 28 along with specular element 27 may be mounted on a housing of an apparatus and by which the element 27 is disposed within a passageway such as like passageway 16. An example of this adaptation is readily apparent with the disclosure of U.S. Pat. No. 4,228,341 in view. In other words, elements 27, 28 need not be limited in their location to the housing 11 and cavity 26 as shown in the drawing.

Also, the feature of universality of rotation of device 10 about an optical or other axis, or about adaptor 20, or vice versa, need not be limited to a device wherein the specular element 27 is exclusively located in the cavity 26. I.e., the universality-of-rotation feature may be incorporated in a device wherein the specular element 27 is disposed within the circumferential or other dimensions of a passageway such as like passageway 16. Adaptation of this feature to state-of-the-art teachings becomes apparent by again referring to the disclosure in U.S. Pat. No. 4,228,341.

INDUSTRIAL APPLICABILITY

As indicated above, device 10 is most suitable at the present time for laser beam surgical operations. However, its use need not be limited thereto.

Pursuant to the requirements of the patent statutes, the invention has been described herein, and exemplified by illustration of an embodiment thereof. Various changes and modifications of such or other embodiments within the skill of the mechanic of the art to which the invention relates or is used in may be made, without falling outside the spirit and scope of the following appended claims.

What I claim as patentably distinct is:

1. An apparatus for directionally controlling transmission of a laser beam or the like to a target area, comprising in combination, a housing having first a chamber with an open terminus for introduction of the beam or the like for transmission therealong, and second a passageway formed by wall means in said housing intersecting the chamber, the passageway open to atmosphere and providing an unobstructed line of sight to the target area for an operator utilizing said apparatus, lens means mounted in the chamber for focusing such beam or the like, a specular element mounted in said housing in alignment with such chamber for directing the beam or the like transmitted through the chamber to atmosphere in the direction of the target area, means mounted on said housing and being operatively connected to said specular element for moving the element, thereby directionally controlling such beam or the like as it is being transmitted in the direction of the target area from said specular element, said moving means being manipulatable exteriorly of said housing, and means for universally mounting and rotating the housing to an adaptor or the like, said mounting and rotating means formed in a body portion of said housing forming such passageway.

2. The apparatus of claim 1 including
a cavity in the housing intersecting the passageway at its opposite extreme to and in alignment with the chamber, the cavity being open to atmosphere in the direction of the target area,
said specular element mounted and disposed in the cavity.

3. The apparatus of claim 1 wherein said mounting and rotating means comprises
means for engaging and disengaging a groove mounted in an adaptor or the like.

4. The apparatus of claim 3 wherein said engaging and disengaging means comprises
at least one piston slidably mounted in a bore of a body portion of said housing forming the passageway, said piston being normally biased in position along a length of said bore forming a slot lying within volumetric dimensions of the passageway, said piston being part of a shaft having a reduced section which when co-extensive with such slot provides for releasing and universal locking of said adaptor to the passageway, the piston in its normally biased position engaging such groove of said adaptor through such slot, and
means for displacing said piston from its normally biased position to cause said reduced section to be co-extensive with such slot and by which such releasing and universal locking is accomplished.

5. The apparatus of claim 4 wherein said displacing means comprises at least said shaft projecting exteriorly of said body portion of said housing.

6. The apparatus of claim 5 including means for biasing said piston to its normal position along the length of the bore forming the slot.

7. The apparatus of claim 4 including means for biasing said piston to its normal position along the length of the bore forming the slot.

8. The apparatus of claim 6 or claim 7 wherein said biasing means comprises a coiled spring in the bottom of the bore acting against the piston and a stopper element on the shaft cooperating with a collar closing off the bore to the exterior of the body portion of said housing.

9. The apparatus of claim 8 including a means for resting a hand or the like mounted on said housing proximate said moving means.

10. The apparatus of claim 9 including
means for introducing nitrogen into the chamber mounted on said housing to cool said lens means.

11. The apparatus of claim 11 including means for clamping the adaptor to the housing.

12. The apparatus of claim 9 wherein said resting means comprises a slip-fitable sleeve with a stem threaded through at least one hole in said sleeve to frictionally grip said housing.

13. The apparatus of claim 12 including
means for introducing nitrogen into the chamber mounted on said housing to cool said lens means.

14. The apparatus of claim 13 including means for clamping the adaptor to the housing.

15. The apparatus of claim 1 or claim 3 or claim 4 or claim 5 or claim 6 or claim 7 including a means for resting a hand or the like mounted on said housing proximate said moving means.

16. The apparatus of claim 15 including
means for introducing nitrogen into the chamber mounted on said housing to cool said lens means.

17. The apparatus of claim 16 including means for clamping the adaptor to the housing.

18. The apparatus of claim 15 wherein said resting means comprises a slip-fitable sleeve with a stem threaded through at least one hole on said sleeve to frictionally grip said housing.

19. The apparatus of claim 18 including
means for introducing nitrogen into the chamber mounted on said housing to cool said lens means.

20. The apparatus of claim 19 including means for clamping the adaptor to the hosuing.

21. The apparatus of claim 8 including means for introducing nitrogen into the chamber mounted on said housing to cool said lens means.

22. The apparatus of claim 21 including means for clamping the adaptor to the housing.

23. The apparatus of claim 1 or claim 3 or claim 4 or claim 5 or claim 6 or claim 7 including scalloped edges in the formation of the passageway and disposed at its terminus nearest the target area to which the beam is directed.

24. The apparatus of claim 23 including means for clamping the adaptor to the housing.

25. The apparatus of claim 3 or claim 4 or claim 5 or claim 6 or claim 7 including means for clamping the adaptor to the housing.

26. The apparatus of claim 15 including means for clamping the adaptor to the housing.

27. The apparatus of claim 18 including means for clamping the adaptor to the housing.

28. In an apparatus for directionally controlling to a target area a reflected beam of light from a specular element disposed in a housing of the apparatus, the specular element being swivable from the exterior of the housing to so control the direction of the reflected beam of light, the housing including an open chamber and an intersecting passageway communicating therewith and being open to atmosphere, the beam of light being focused by a lens in the chamber and thereafter being transmitted through the chamber to the passageway wherein the specular element is disposed, the improvement comprising
means for universally mounting and rotating the housing to an adaptor or the like,
said mounting and rotating means formed in a body portion of the housing forming the passageway.

29. In the apparatus of claim 28, said mounting and rotating means comprising
means for engaging and disengaging a groove in an adaptor or the like.

30. The engaging and disengaging means of claim 29 comprising
  at least one piston slidably mounted in a bore of the body portion of the housing forming the passageway, said piston being normally biased in a position along a length of the bore forming a slot lying within volumetric dimensions of the passageway, said piston being part of a shaft having a reduced section which when co-extensive with such slot provides for releasing and universal locking of said adaptor to the passageway, the piston in its normally biased position engaging such groove of said adaptor through such slot, and
  means for displacing said piston from its normally biased position to cause said reduced portion to be co-extensive with such slot and by which such releasing and universal locking is accomplished.

31. The displacing means of claim 30 comprising at least said shaft projecting exteriorly of said body portion of said housing.

32. Claim 31 but also including means for biasing said piston to its normal position along the length of the bore forming the slot.

33. Claim 30 but also including means for biasing said piston to its normal position along the length of the bore forming the slot.

34. Claim 32 or claim 33 wherein said biasing means comprises a coiled spring in the bottom of the bore acting against the piston and a stopper element on the shaft cooperating with a collar closing off the bore to the exterior of the body portion of the housing.

35. In the apparatus of claim 34, means for clamping the adaptor to the housing.

36. In the apparatus of claim 29 or claim 30 or claim 31 or claim 27 or claim 28, means for clamping the adaptor to the housing.

37. In an apparatus for directionally controlling to a target area a reflected beam of light from a specular element disposed in a housing, the specular element being swivable from the exterior of the housing to so control the direction of the reflected beam of light, the housing including an open chamber and an intersecting passageway communicating therewith and being open to atmosphere, the beam of light being focused by a lens in the chamber and thereafter being transmitted through the chamber to the passageway,
  the improvement comprising
  a cavity in the housing in alignment with the chamber but being separated therefrom by the passageway with which it communicates,
  said specular element being mounted in the cavity, the cavity being open to atmosphere in the direction of the target area for transmission of the reflected beam to the target area,
  thereby eliminating obstruction in the passageway that otherwise would interfere with line of sight for an operator of the apparatus observing the direction of the reflected beam of light through the passageway.

38. In the apparatus of claim 37, the improvement including
  means for universally mounting and rotating the housing to an adaptor or the like.

39. In the apparatus of claim 38, said mounting and rotating means comprising
  means for engaging and disengaging a groove mounted in an adaptor or the like.

40. In the apparatus of claim 37 or claim 38 or claim 39, means included for introducing nitrogen into the chamber to cool the lens mounted and disposed therein.

41. In the apparatus of claim 40, means for clamping the adaptor to the housing.

42. In the apparatus of claim 38 or claim 39, means for clamping the adaptor to the housing.

* * * * *

UNITED STATES PATENT AND TRADEMARK OFFICE
CERTIFICATE OF CORRECTION

PATENT NO. : 4,494,540
DATED : January 22, 1985
INVENTOR(S) : Robert C. Erb

It is certified that error appears in the above-identified patent and that said Letters Patent are hereby corrected as shown below:

Col. 9, line 36, --a-- is to be read immediately after "in".

Col. 10, line 1, "11" [following the word "claim"] is cancelled, and --10-- substituted therefor.

Col. 11, line 35, "27" is cancelled and --32-- substituted therefor; "28" is cancelled and --33-- is substituted therefor.

Signed and Sealed this

Seventh Day of May 1985

[SEAL]

*Attest:*

DONALD J. QUIGG

*Attesting Officer*     *Acting Commissioner of Patents and Trademarks*